(12) United States Patent
Nishimura et al.

(10) Patent No.: US 6,431,261 B2
(45) Date of Patent: Aug. 13, 2002

(54) SHELL AND TUBE TYPE HEAT EXCHANGER

(75) Inventors: Takeshi Nishimura, Himeji; Yukihiro Matsumoto, Kobe; Daisuke Nakamura, Himeji; Masakatsu Mori; Osamu Dodo, both of Hyogo, all of (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/733,679

(22) Filed: Dec. 8, 2000

(30) Foreign Application Priority Data

Dec. 28, 1999 (JP) .......................................... 11-374636

(51) Int. Cl.[7] ................................................. F28D 7/00
(52) U.S. Cl. ..................... 165/81; 165/159; 122/510; 122/4 D; 285/285.1; 285/295.1
(58) Field of Search .................... 165/158, 159, 165/81, 82; 122/510; 422/197; 285/285.1

(56) References Cited

U.S. PATENT DOCUMENTS

| | | | |
|---|---|---|---|
| 1,439,283 A | * 12/1922 | Astrom | 165/82 |
| 1,921,988 A | * 8/1933 | Govers | 165/82 |
| 2,232,936 A | * 2/1941 | Bimpson | 165/82 |
| 3,915,124 A | * 10/1975 | Kuhn, Jr. et al. | 122/115 |
| 4,249,593 A | * 2/1981 | Bieberbach et al. | 165/158 |
| 4,256,783 A | * 3/1981 | Takada et al. | 422/197 |
| 4,431,049 A | * 2/1984 | Zamma et al. | 165/83 |
| 4,434,840 A | * 3/1984 | Porowski et al. | 165/82 |
| 4,511,162 A | * 4/1985 | Broyles | 285/226 |
| 4,526,409 A | * 7/1985 | Schaefer | 285/114 |
| 4,641,608 A | * 2/1987 | Waryasz | 165/81 |
| 4,837,360 A | 6/1989 | Kadowaki et al. | 562/546 |
| 5,101,892 A | * 4/1992 | Takeuchi et al. | 165/159 |
| 5,355,945 A | * 10/1994 | Sanz et al. | 165/159 |
| 5,378,026 A | * 1/1995 | Ninacs et al. | 285/47 |
| 5,542,715 A | * 8/1996 | Mantoan et al. | 285/226 |
| 5,615,738 A | * 4/1997 | Cameron et al. | 165/159 |
| 5,739,391 A | 4/1998 | Ruppel et al. | 562/532 |
| 5,775,414 A | * 7/1998 | Graham | 165/158 |
| 5,821,390 A | 10/1998 | Ruppel et al. | 562/470 |

* cited by examiner

Primary Examiner—Henry Bennett
Assistant Examiner—Terrell McKinnon
(74) Attorney, Agent, or Firm—Mathews, Collins, Shepherd & McKay, P.A.

(57) ABSTRACT

The temperature distribution in a shell and tube type heat exchanger having an expansion joint is uniformized by improving the circulation efficiency of fluid in the shell side. The uniformization is attained by the heat exchanger having an invasion-preventing plate against the fluid in the shell side attached to the expansion joint installed around the periphery of the shell, and a method of catalytic gas phase oxidation reaction that uses the heat exchanger.

11 Claims, 2 Drawing Sheets

SHELL AND TUBE TYPE HEAT EXCHANGER

BACKGROUND OF THE INVENTION

1. Field of the Invention

The present invention relates to a shell and tube type heat exchanger, a method for catalytic gas phase oxidation that uses the heat exchanger, and a reactor that uses the heat exchanger.

2. Description of the Related Art

In a shell and tube type reactor, a reaction is carried out by charging a heat medium such as molten salt, etc. into a shell chamber having a bundle of reaction tubes therein, circulating the medium, and simultaneously feeding a gaseous raw material for the reaction into the reaction tubes; and the heat generated in the reaction is absorbed by use of the above-mentioned heat medium to thereby maintain the predetermined conditions of a catalytic gas phase oxidation reaction.

Examples of the catalytic gas phase oxidation reaction include reactions producing acrolein from propylene, methacrolein from isobutylene, maleic anhydride frombenzene, phthalic anhydride from xylene and/or naphthalene, acrylic acid from acrolein, and methacrylic acid from methacrolein.

These catalytic gas phase oxidation reactions are accompanied by an extremely large amount of heat, and an abnormal high temperature zone (hot spot) is often locally formed. The reactor might be damaged by thermal strain caused by such heat.

Particularly, in a reactor equipped with a partition sheet that has a plurality of chambers having temperature difference each other, if the temperature difference between the two chambers divided by the partition sheet is great, a big thermal stress is formed in the place. When the temperature difference exceeds a level, the reactor may be broken because of the occurrence of the thermal stress exceeding the maximum allowable stress of the shell. For this reason, in order to decrease the influence on the reactor by heat, an expansion joint that can absorb the distortion that occurs because of the rise or the descent of the temperature of fluid in the shell side is adopted. The joint is formed on the shell of the reactor in the manner in which the inner surface of a long band having a semicircle-like cross section is turned toward the inside of the reactor such that the band makes one round almost horizontally around the shell, and each of the top end and the bottom end of the quasi-semicircle of the long band is connected by use of a known method such as welding to the shell of the reactor which was almost horizontally cut.

However, there remains a drawback in this method that the fluid in the shell side invades the expansion joint to thereby disturb the moving direction of the fluid, and as a result the heat generated in the reaction cannot be sufficiently removed.

Moreover, as one of drawbacks of a catalyst containing molybdenum such as a complex oxide catalyst including molybdenum-bismuth-iron, the molybdenum component sublimes easily when steam exists in the reaction system, and particularly, the sublimation of the molybdenum component is promoted at a high temperature (JP-A-55-113730). In addition, in a reaction accompanied by heat such as the oxidation reaction of propylene, an abnormal high temperature zone (hot spot) is locally formed in the catalytic layer, which raises the conditions where the molybdenum is more easily sublimed as a result. Furthermore, these sublimed molybdenum component is deposited in the part of lower temperature to thereby increase the pressure drop of the catalytic layer. As a result, the hot spot additionally increases. That is, there remains a problem of difficulty in controlling the reaction temperature.

SUMMARY OF THE INVENTION

As a consequence, the present invention has been accomplished in view of the foregoing.

Objects of the present invention are to provide a shell and tube type heat exchanger in which the movement of the fluid in the shell side is not disturbed by the expansion joint; a method for the catalytic gas phase oxidation reaction that uses a heat exchanger where the temperature distribution of the fluid in the shell side is uniformed as a whole; and a reactor that uses the heat exchanger.

The object of the present invention is attained by a shell and tube type heat exchanger characterized by attaching an invasion-preventing plate against the fluid in the shell side to the expansion joint portion installed around the periphery of the shell.

Another object of the present invention is attained by a method of the catalytic gas phase oxidation reaction characterized by using the above-mentioned shell and tube type heat exchanger.

The further object of the present invention is attained by a reactor characterized in that the shell and tube type heat exchanger is partitioned into two or more chambers by use of one or more shield sheets transversely of the length of the reaction tube.

According to the present method, it is possible to provide a shell and tube type heat exchanger having a uniformed temperature distribution therein because the fluid in the shell side can be moved, without disturbing by the expansion joint portion, by installing the invasion-preventing plate against the fluid in the shell side.

According to the present invention, it is also possible to uniform the temperature distribution of the fluid in the shell side of a reactor, and extend the lifetime of the whole catalyst because the pressure drop in the reaction tube after the reaction is done for a long term can be uniformized, and at the same time the amount of sublimation of the catalyst constituents such as molybdenum can be uniformized.

According to the present invention, it is possible to provide a reactor having a uniformed temperature distribution in the reactor because the shell of a shell and tube type heat exchanger is partitioned into two or more chambers by use of one or more shield sheets transversely of the length of the reaction tube, and the movement of the fluid in the shell side is not disturbed by the expansion joint portion when different reactions are carried out corresponding to each of the chambers, by installing a invasion-preventing plate against the fluid in the shell side.

The above and other objects, features and advantages of the present invention will become clear from the following description of the preferred embodiments.

BRIEF DESCRIPTION OF DRAWINGS

The accompanying drawing incorporated in and forming a part of the specification, illustrates several aspects of the present invention, and together with the description serve to explain the principles of the invention. In the drawings.

DESCRIPTION OF THE PREFERRED EMBODIMENTS

Figure 1:
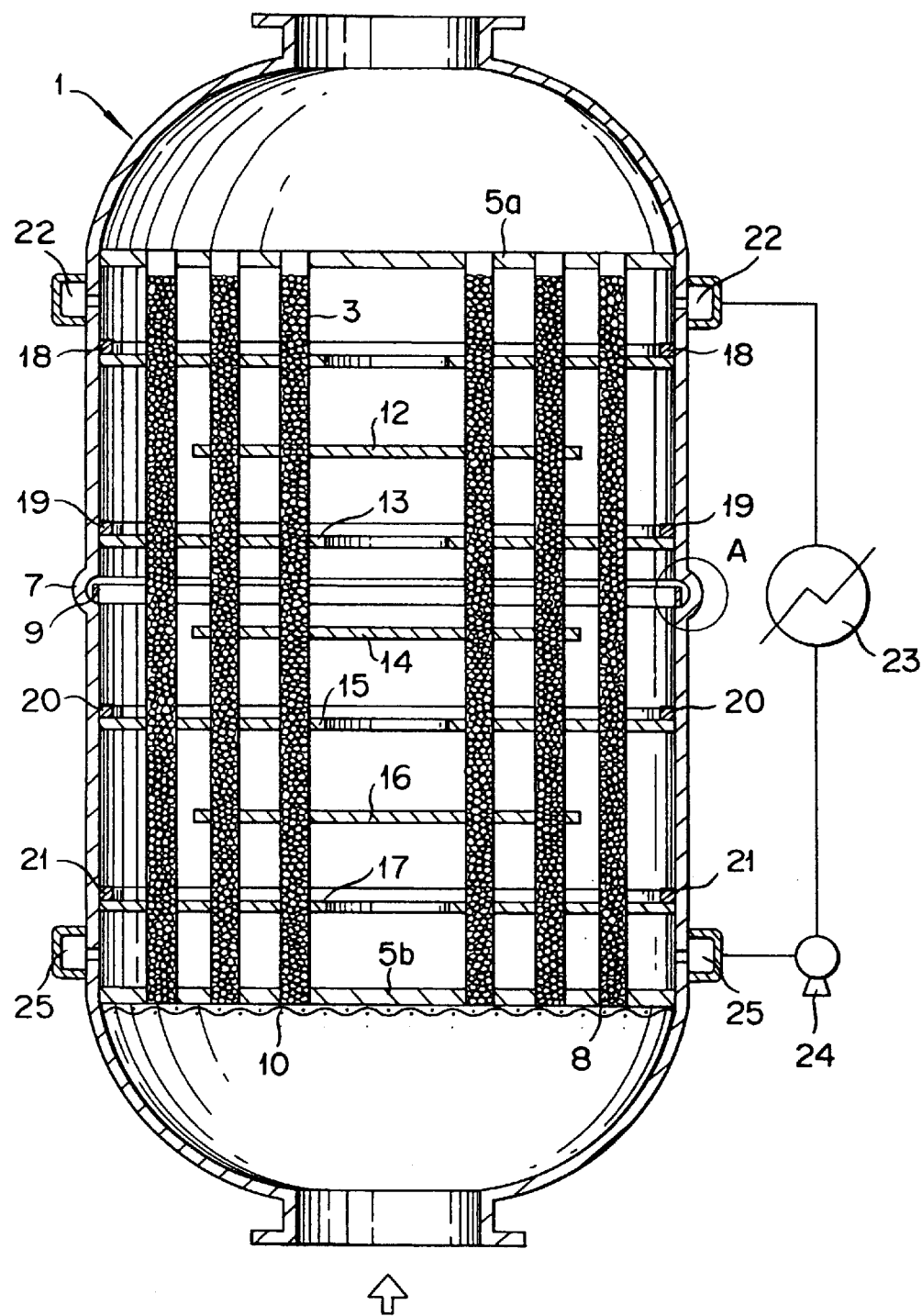
FIG. 1 is a vertical sectional view of an example of the vertical shell and tube type reactor of the present invention.

As shell and tube type heat exchangers used for the present invention, any heat exchanger can be used without being particularly limited, as long as it is vertical or horizontal, has a structure in which a lot of heat exchanger tubes are arranged in a cylindrical shell, and uses a system in which the heat exchange is performed between the inside and the outside of the heat exchanger tubes. Preferably, the heat exchanger is vertical, and it is preferable to use the heat exchanger as a reactor of a catalytic gas phase oxidation reaction, etc. In addition, the heat exchanger is equipped more preferably with annular conduits having a plurality of openings to introduce and withdraw a fluid in the shell side such as a heat medium from the periphery of the reactor, and has the means to uniform the temperature distribution near a horizontal plane on which the gateway of the fluid in the shell side in the reactor exists. It is preferable to install annular conduits in the vicinity of each the upper and lower tube sheets, from the viewpoint of uniforming the temperature distribution of the fluid in the shell side.

An expansion joint that can absorb the distortion that occurs because of the rise or the descent of the temperature of heat medium, etc. is installed in the heat exchanger. The joint is formed in the manner in which the inner surface of a long band having a semicircle-like cross section is turned toward the inside of the heat exchanger such that the band makes one round around the shell, and each of the top end and the bottom end of the quasi-semicircle is connected, by use of a known method such as welding, to the shell of the heat exchanger which was almost horizontally cut. To increase the flexibility of shell of the heat exchanger, such an expansion joint can be fabricated with a board whose material is the same as that of the shell. A plurality of expansion joints can be installed if necessary. Particularly, the expansion joint is effective when the temperature difference between the fluid in the shell side and the fluid in the tube section is large, and the difference of the coefficient of thermal expansion between the tube material and the shell material is extremely large.

Invasion-preventing plates against the fluid in the shell side are not particularly limited, as long as the plate has the function of preventing the invasion of the fluid such as a heat medium into the expansion joint installed around the periphery of the shell. Preferably, the invasion-preventing plate is typically a plate-shaped matter that covers the whole or almost the whole expansion joint, and the plate is fixed, by use of a known method such as welding, near any one of the two connection portions between the expansion joint and the shell of the reactor. Typically, the plate is preferably fixed, on the upper stream side to the flow direction of the fluid in the shell side, in the vicinity of the two connection portions not to disturb the movement of the circulating fluid in the shell side. The fixation can extend all around the periphery of the expansion joint, but also be done using a method of a partial fixation if the invasion-preventing plate can be fixed. Since such installation of the invasion-preventing plate against the fluid in the shell side disturbs the invasion of the fluid into the expansion joint, the fluid in the shell side can smoothly flow in the heat exchanger.

Baffle plates for chiefly horizontally moving the fluid in the shell side are preferably installed into the heat exchanger. Here, the baffle plate is one of known baffle plates such as a disc type circular plate, donut type circular plate having a hole, segmented type, half-moon type, and orifice type baffle plate, or one or a combination of two or more of them.

In addition, a seal plate is preferably installed in the space between the shell of the heat exchanger and the rim of the donut type circular plate for instance. The seal plate is not particularly limited if the plate covers the gap, but may include an annular plate. The seal plate can adopt, for instance, a known method of fixing it by welding the plate to the shell and then connecting the plate with the baffle plate with a bolt. The seal plate can be installed on the top or the bottom of the baffle plate (in FIG. 1 which is described after, the plate is installed on the upper part of the baffle plate.). The installation of the seal plate allows the fluid in the shell side to travel along the baffle plate as designed to reduce the temperature distribution of the fluid in the shell side and make it possible that the reaction temperature may be controlled in the narrower range than was previously.

These shell and tube type heat exchangers can be used for a catalytic gas phase oxidation reaction because, even if a reaction generates heat, they in particular a vertical shell and tube type heat exchanger can effectively absorb such heat.

Heat exchangers having a divided chamber, fabricated by partitioning the shell of the above-mentioned heat exchanger into two or more chambers by use of one or more shield sheets transversely of the length of the reaction tubes, can be used for especially the catalytic gas phase oxidation. When the shell is partitioned into two or more chambers by use a shield sheet, from the viewpoint of reducing the temperature distribution in each chamber, the chambers are preferably partitioned by use of an intermediate tube sheet such that the fluid in the shell does not leak as much as possible. The intermediate tube sheet has a plurality of grooves, e.g., two grooves, and the reaction tube is firmly fixed through the groove by a pipe-expanding method.

More preferably, the temperature difference of the fluid in the shell side (heat medium) between the partitioned chambers is 100° C. or less (zero is not included) from the viewpoint of avoiding the occurrence of the thermal stress.

In such a partitioned reactor, an invasion-preventing plate against the fluid in the shell side is preferably attached to the expansion joint portion installed around the periphery of the shell to at least one chamber, more preferably, to all the chambers.

Each the chambers partitioned in this way corresponds to a heat exchanger, so that each the chambers is preferably equipped with one set of the annular conduits, the baffle plates, and the seal plates, etc. properly in the same way the heat exchanger is equipped.

Hereafter, the present invention will be described in detail with reference to the drawings. An explanation is given regarding the vertical shell and tube type reactor as a representative. However, the present invention is not limited only to this embodiment.

Figure 2:
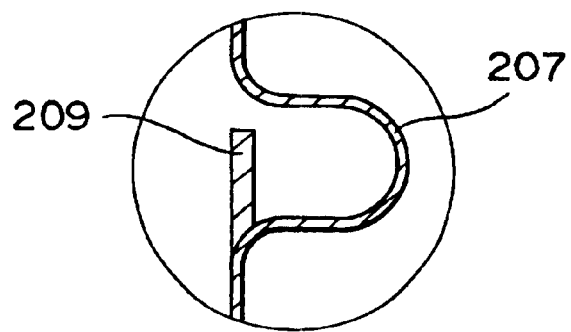
FIG. 2 is an enlarged view of part A of FIG. 1.

FIG. 1 is a vertical sectional view of an example of the vertical shell and tube type reactor of the present invention. In FIG. 1, a lot of reaction tubes 3 are installed in a reactor 1, and each the reaction tube is fixed to an upper tube sheet 5a with the top end thereof and to a lower tube sheet 5b with the bottom end thereof by means of a known method such as pipe-expanding method or welding. From the center part of the reactor 1, the reaction tubes are removed in order to improve the flow of known fluid such as molten salt in the vertical direction, but the reaction tubes can be closely arranged therein if necessary. In the reactor 1, an expansion joint 7 is installed all around the periphery of the shell. In the expansion joint 7, an invasion-preventing plate 9 against the fluid in the shell side is installed. FIG. 2 is an enlarged view of part A of FIG. 1. The invasion-preventing plate 209 is installed on the bottom part of opening of the expansion joint 207 to prevent the invasion of the fluid into the expansion joint. However, the invasion-preventing plate 209 is not fixed completely covering the expansion joint 207, so that the fluid in the shell side enters the expansion joint 207 through the upper part of the invasion-preventing plate 209.

Moreover, in the reactor 1, baffle plates are installed in the order, from the top, of a donut type plate 11, a disc type plate 12, a donut type plate 13, a disc type plate 14, a donut type plate 15, a disc type plate 16, and a donut type plate 17. Seal plates 18, 19, 20, and 21 such as annular plate each are installed between the rims of the donut type plates 11, 13, 15, and 17, and the shell of the reactor 1.

Reaction tubes 3 are filled with a required amount of a catalyst 8 for the catalytic gas phase oxidation reaction. Before charging the catalyst thereinto, a wire mesh or receiver 10 for preventing the catalyst 8 from falling is placed on the bottom end of the reaction tubes 3. Before charging the catalyst thereinto, if necessary, an inert refractory substance for example granules is optionally charged thereinto in order to preheat the raw material gas during the reaction.

Examples of the inactive refractory substance may include α-alumina, alundum, mullite, carborundum, stainless steel, silicon carbide, steatite, earthenware, porcelain, iron, and various kinds of ceramic materials.

As the catalysts, conventional catalysts may be cited, but may include the following.

Examples of a catalyst for producing acrolein from a propylene-containing gas may include the catalyst represented by the formula:

Mo$_a$—Bi$_b$—Fe$_c$—A$_d$—B$_e$—C$_f$—D$_g$—O$_x$ wherein
Mo, Bi, and Fe respectively denote molybdenum, bismuth, and iron,
A denotes at least one element selected from the group consisting of nickel and cobalt,
B at least one element selected from the group consisting of alkali metals and thallium,
C at least one element selected from the group consisting of phosphorus, niobium, manganese, cerium, tellurium, tungsten, antimony, and lead,
D at least one element selected from the group consisting of silicon, aluminum, zirconium, and titanium,
O oxygen, and
a, b, c, d, e, f, g, and x respectively denote the atomic ratios of Mo, Bi, Fe, A, B, C, D, and O which fall in the respective ranges of b=0.1–10, c=0.1–10, d=2–20, e 32 0.001–5, f=0–5, g=0–30, and x the value decided by the states of oxidation of the relevant elements when a=12 is fixed.

Then, examples of a catalyst for producing acrylic acid from an acrolein-containing gas may include the catalyst represented by the formula:

Mo$_a$—V$_b$—W$_c$—Cu$_d$—A$_e$—B$_f$—C$_g$—O$_x$ wherein
Mo denotes molybdenum, V vanadium, W tungsten, Cu copper,
A at least one element selected from the group consisting of antimony, bismuth, tin, niobium, cobalt, iron, nickel, and chromium,
B at least one element selected from the group consisting of alkali metal, alkaline earth metals, and thallium,
C at least one element selected from the group consisting of silicon, aluminum, zirconium, and cerium,
O oxygen, and
a, b, c, d, e, f, g, and x denote the atomic ratios respectively of Mo, V, W, Cu, A, B, C, and O which fall in the respectively ranges of b=2–14, c=0–12, d=0.1–5, e=0–5, f=0–5, g=0–20, and x the value decided by the states of oxidation of the relevant elements when a=12 is fixed.

To be specific, a catalyst for producing methacrolein from isobutylene-containing gas is preferred to be the composition represented by the formula:

Mo$_a$—W$_b$—Bi$_c$—Fe$_d$—A$_e$—B$_f$—C$_g$—D$_h$—O$_x$ wherein
Mo, W, and Bi respectively denote molybdenum, tungsten, and bismuth,
Fe denotes iron,
A nickel and/or cobalt,
B at least one element selected from the group consisting of alkali metals, alkaline earth metals, and thallium,
C at least one element selected from the group consisting of phosphorus, tellurium, antimony, tin, cerium, lead, niobium, manganese, and zinc,
D at least one element selected from the group consisting of silicon, aluminum, titanium, and zirconium,
O oxygen, and
a, b, c, d, e, f, g, h, and x respectively denote the numbers of atoms of Mo, W, Bi, Fe, A, B, C, D, and 0, which fall respectively in the ranges of b=0–10, c=0.1–10, d=0.1–20, e=2–20, f=0.001–10, g=0–4, h=0–30, and x assumes the numerical value decided by the states of oxidation of the relevant elements where a=12 is fixed.

A catalyst for producing methacrylic acid from a methacrolein-containing gas is not particularly restricted so long as it comprises one or more oxidation catalysts containing molybdenum and phosphorus as main components. It is preferred to be a phosphomolybdic acid type heteropoly acid or a metal salt thereof. Specifically, it is preferred to be the composition represented by the formula:

Mo$_a$—P$_b$—A$_c$—B$_d$—C$_e$—D$_f$—O$_x$ wherein
Mo denotes molybdenum,
P denotes phosphorus,
A denotes at least one element selected from the group consisting of arsenic, antimony, germanium, bismuth, zirconium, and selenium,
B at least one element selected from the group consisting of copper, iron, chromium, nickel, manganese, cobalt, tin, silver, zinc, palladium, rhodium, and tellurium,
C at least one element selected from the group consisting of vanadium, tungsten, and niobium,
D at least one element selected from the group consisting of alkali metals, alkaline earth metals, and thallium,
O oxygen, and
a, b, c, d, e, f, and x respectively denote the atomic ratios respectively of Mo, P, A, B, C, D, and O, which falls in the ranges of b=0.5–4, c=0–5, d=0–3, e=0–4, f=0.01–4, and x denotes the numerical value decided by the state of oxidation of the relevant elements where a=12 is fixed.

Incidentally, the catalysts that form the upstream side catalyst and downstream side catalyst beds, do not need to be a simple catalyst each. For example, plural kinds of catalysts different in activity may be adopted, when necessary, such catalysts may be diluted with an inactive material such as an inactive carrier.

The shape of catalysts is not particularly restricted. The catalyst may be in the shape of Raschig rings, spheres, cylinders, and rings, for example. As the method for forming the catalyst of such a shape, carried molding, extrusion molding, and tablet molding may be adopted. Further, the catalyst obtained by depositing a catalytic substance on a refractory carrier is useful.

The conditions for the gas phase catalytic oxidation of a raw material gas containing propylene or isobutylene with molecular oxygen may be those of any known methods available for the reaction. When acrolein is produced by oxidizing propylene in the presence of catalysts, for example, the propylene concentration in the raw material gas is in the range of 3–15% by volume, the ratio of the molecular oxygen to the propylene is in the range of 1–3, and the remainder of the raw material gas comprises nitrogen, steam, carbon oxides, and propane etc.

Though air is advantageously used as the source for the molecular oxygen, an oxygen-enriched air or pure oxygen may be used as occasion demands. Oxidation reactions are performed by a one-pass or recycling method. Preferably, the reaction temperature may be in the range of 250° C. –450° C., the reaction pressure in the range of atmospheric pressure to five atmospheres, and the space velocity in the range of 500–3000 $h^{-1}$ (STP: Standard Temperature and Pressure).

Then, the acrolein-containing gas produced by the reaction mentioned above, if necessary to add a secondary air, secondary oxygen or steam, may be supplied to the reactor at a reaction temperature (the temperature of the heat medium in the reactor) in the range of 100–380° C., preferably 150–350° C., at a space velocity in the range of 300–5,000 $h^{-1}$ (STP) so as to produce acrylic acid.

In the production of methacrolein by the reaction of gas phase catalytic oxidation of an isobutylene-containing raw-material gas in the presence of a catalyst, the isobutylene concentration in the raw material gas may be in the range of 1–10% by volume, the concentration of molecular oxygen to isobutylene is in the range of 3–20% by volume, a steam content is in the range of 0–60% by volume, and the remainder comprises nitrogen, steam, and carbon oxides. Though air is advantageously used as the source for the molecular oxygen, an oxygen-enriched air or pure oxygen may be used as occasion demands. Preferably, the reaction temperature is in the range of 250° C. –450° C., the reaction pressure in the range of atmospheric pressure to five atmospheres, and the space velocity in the range of 300–5000 $h^{-1}$ (STP).

Further, the methacrolein-containing gas produced by the reaction, if necessary to add a secondary air, secondary oxygen or steam, is supplied to a reactor for example at a reaction temperature in the range of 100–380° C., preferably 150–350° C., at a space velocity in the range of 300–5,000 $h^{-1}$ (STP) so as to produce methacrylic acid.

The fluid in the shell side is withdrawn from an annular conduit 22 installed around the outer periphery of a reactor 1 and having a plurality of openings that lead to the reactor 1, and then cooled by a heat exchanger 23. The cooled fluid is introduced into the reactor 1 from an annular conduit 25 installed around the outer periphery of the reactor 1 and having a plurality of openings that lead to the reactor 1, by use of a known pump 24 such as a centrifugal or axial-flow pump. The fluid enters the reactor 1 from almost all around the perimeter of the inner periphery of the reactor 1, contacting the bundle of reaction tubes 3, and absorbing heat when the reaction is exothermic, travels toward the center of the reactor 1, and then goes up through the hole of the donut type plate 17. Further, the fluid travels almost horizontally along the disc type plate 16 toward almost the whole area of the inner periphery portion of the reactor 1, contacting the bundle of reaction tubes 3, and absorbing the heat of the reaction, and then goes up from the outer periphery of the disc type plate 16. Because the seal plate 21 is installed around the outer periphery of the donut type plate 17, there is no gap between the reactor 1 and the plate 17. Therefore, the fluid travels along the donut type and disc type plates without leaking, and can uniform the temperature distribution in the reactor 1. In addition, the invasion-preventing plate 9 is also installed near the expansion joint 7, so that the fluid in the shell side travels along the flow of the fluid without invading the expansion joint 7, and can contribute to the reduction of the temperature distribution in the reactor 1. The fluid in the side travels toward the annular conduit 22, then repeating this manner.

In this embodiment, the raw material gas is allowed to flow from the lower portion to the upper portion of the reactor 1, and the fluid in the shell side is allowed to flow concurrently with the raw material gas. However, the raw material gas and the fluid in the shell side can be also allowed to flow in any direction.

Furthermore, by use of the reactor according to the present invention, maleic anhydride can be also produced from a benzene-or butane-containing gas as the raw material in the presence of a known catalyst by means of a known reaction system; and phthalic anhydride can be also produced from a xylene and/or naphthalene-containing gas as the raw material in the presence of a known catalyst by means of a known reaction system.

Additionally, in a more complex reactor that is partitioned into upper and lower chambers by use of intermediate tube sheets and partition sheets, the effect of expansion joint is more remarkable, and at the same time the effects of installation of invasion-preventing plates against the fluid in the shell side and seal plates are confirmed.

EXAMPLES

The present invention will be described and illustrated by way of examples below. However, the invention is not limited only to these examples.

Example 1 and Comparative Example 1

A vertical shell and tube type heat exchanger having 6,400 pieces of steel-tubes having a length of 4 m, an internal diameter of 25.0 mm, and an external diameter of 29.0 mm, a baffle plate consisting of a disc type plate and a donut type plate, and an expansion joint which was installed in the shell was used as a reactor. A catalyst that is chiefly used for producing acrolein from propylene was charged into the reactor in a height of 3,000 mm, and the pressure drop in the reactor was measured by use of air having a main pressure of 98,066.5 Pa gauge (1.0 kg/cm² gauge) at a rate of 35 N-liters/min. The obtained results are shown in Table 1 below.

A mixture of potassium nitrate (50 wt. %) and sodium nitrite (50 wt. %) was used as a heat medium, and was circulated from the lower portion to the upper portion in the reactor in an amount of 3,000 m³/hr by use of a pair of an upper and lower annular conduits.

Into the reactor was fed the raw material gas consisting of propylene (7 vol. %), oxygen (12.6 vol. %), steam (10 vol. %), and nitrogen etc. (70.4 vol. %) such that the catalyst-contacting time is 2.5 seconds. The apparatus used in Example 1 is shown in FIG. 1 (However, the reactor used in Example 1 did not have a seal plate in the baffle plate).

The catalyst used here was prepared by using the method and the raw material composition (containing no oxygen) that are shown in a known method:

Purewater (1,500 liters) was heated, and stirred. Into the water were added and dissolved ammonium molybdate (1,000 kg) and ammonium paratungstate (64 kg). To the obtained mixture was added dropwise an aqueous nitrate solution that had been prepared in the following method. Cobalt nitrate (687 kg) was added into pure water (1,000 liters), and dissolved therein. Ferric nitrate (191 kg) was added into pure water (300 liters), and dissolved therein. Bismuth nitrate (275 kg) was added into an aqueous solution containing pure water (300 liters) and a concentrated nitric acid (60 liters), and dissolved therein. These obtained three nitrate solutions were mixed to obtain the above-described aqueous nitrate solution. Subsequently, to the obtained mixture was added an aqueous solution containing a 20 wt. % silica sol solution (142 kg), potassium nitrate (2.9 kg), and pure water (150 liters) to obtain a suspension. The obtained suspension was heated, mixed, evaporated to dryness, and dried, and then the obtained mixture was pulverized to obtain a powder. The above-mentioned procedure was repeated, to obtain a required amount of the catalyst.

The obtained powder was molded into cylinder-shaped molded products having a diameter of 5 mm. The obtained molded products were calcined at 460° C. for 6 hrs in a stream of air to obtain a catalyst (the catalyst composition (molar ratio): Mo 12, Bi 1.2, Fe 1, Co 5, W 0.5, Si 1, and K 0.06).

Figure 3:
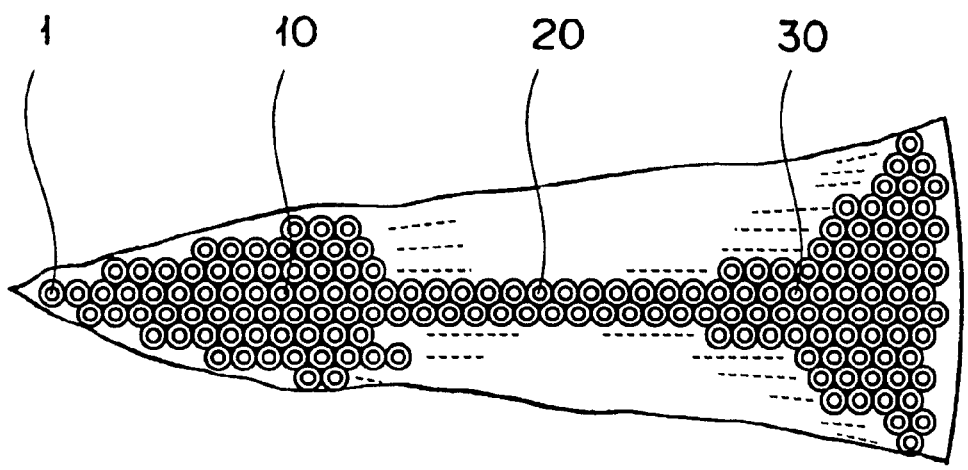
FIG. 3 is an explanatory view of a partially cutaway traverse cross section of the reactor to explain the relation between reaction tubes and the reaction tube numbers.

FIG. 3 is an explanatory view of a partially cutaway traverse cross section of the reactor to explain the relation between the reaction tube and the reaction tube number. In FIG. 3, the reaction tube numbers were assigned in the order from the center radially of the reactor to the shell side.

An oxidation reaction of propylene was continued for 8,000 hrs under the conditions in which the invasion-preventing plate in the expansion joint portion was used (Example 1) or not used (Comparative Example 1). The reaction was stopped, and the pressure drops in the reaction tubes were measured under the same conditions. The obtained results are shown in Table 1.

TABLE 1

Pressure drop (unit: Pa (mm H$_2$O))

|  | Before reaction | After reaction continued for 8,000 hrs | |
| --- | --- | --- | --- |
| Seal plate on baffle plate | — | Not using | Not using |
| Invasion-preventing plate on expansion joint | — | Using | Not using |
| Reaction tube 1 | 18632 (1900) | 20407 (2081) | 21466 (2189) |
| Reaction tube 11 | 19005 (1938) | 20083 (2048) | 21142 (2156) |
| Reaction tube 21 | 18367 (1873) | 19936 (2033) | 20338 (2074) |
| Reaction tube 31 | 19171 (1955) | 19926 (2032) | 19809 (2020) |
| Reaction tube 38 | 18210 (1857) | 19240 (1962) | 18789 (1916) |

In the reaction of Example 1 where the 10 invasion-preventing plate in the expansion joint portion was used, almost the same amount of white needle crystals was shown in the catalytic layer in all the reaction tubes. On the other hand, in the reaction of Comparative Example 1 without the invasion-preventing plate, the amount of white needle crystals deposited in the catalytic layer was found to have increased in the order from the reaction tube 38 toward the reaction tube 1. The pressure drop was found to have increased as the amount of these needle crystals increased. These needle crystals proved to be molybdenum oxide after analysis.

The ratios of increase in the pressure drop calculated based on the results shown in Table 1 are shown in Table 2.

TABLE 2

Ratio of increase in pressure drop (Pressure drop before reaction: 1).

| Invasion-preventing plate in expansion joint | Using | Not using |
| --- | --- | --- |
| Reaction tube 1 | 1.01 | 1.15 |
| Reaction tube 11 | 1.06 | 1.11 |
| Reaction tube 21 | 1.09 | 1.11 |
| Reaction tube 31 | 1.04 | 1.03 |
| Reaction tube 38 | 1.06 | 1.03 |

As is apparent from Table 2, using the invasion-preventing plate in the expansion joint portion relatively reduces the pressure drop, and additionally uniforms the pressure drop.

Example 2

The oxidation reaction of propylene was continued for 8,000 hrs under the same conditions as in Example 1 except the conditions concerning the seal plate and the invasion-preventing plate in the expansion joint portion, and then the pressure drops in the reaction tubes were measured under the same conditions after the reaction was stopped. The obtained results are shown in Table 3. The apparatus used in Example 2 is shown in FIG. 1.

TABLE 3

Pressure drop (unit: Pa (mm H$_2$O))

|  | Before reaction | After reaction continued for 8,000 hrs | |
| --- | --- | --- | --- |
| Seal plate on baffle plate | — | Using | Not using |
| Invasion-preventing plate on the expansion joint | — | Using | Not using |
| Reaction tube 1a | 18632 (1900) | 19544 (1993) | 21466 (2189) |
| Reaction tube 11a | 19005 (1938) | 20074 (2047) | 21142 (2156) |
| Reaction tube 21a | 18367 (1873) | 19485 (1987) | 20338 (2074) |
| Reaction tube 31a | 19171 (1955) | 20024 (2042) | 19809 (2020) |
| Reaction tube 38a | 18210 (1857) | 19171 (1955) | 18789 (1916) |

In the reaction where the seal plate in the baffle plate portion, and the invasion-preventing plate in the expansion joint portion were used, almost the same amount of white needle crystals was shown in the catalytic layer in all the reaction tubes. On the other hand, in the reaction without these preventing plates, the amount of white needle crystals deposited in the catalytic layer was found to have increased in the order from the reaction tube 38a (the position of 38a corresponds to the position of 38 in FIG. 3, and 1a is the same) toward the reaction tube 1a. The pressure drop was found to have increased as the amount of these needle crystals increased. The needle crystals proved to be molybdenumoxide.

The ratios of increase in the pressure drop calculated based on the results shown in Table 3 are shown in Table 4.

TABLE 4

Ratio of increase in pressure drop
(Pressure drop before reaction: 1).

| Seal plate and Invasion-preventing plate | Using | Not using |
| --- | --- | --- |
| Reaction tube 1a | 1.05 | 1.15 |
| Reaction tube 11a | 1.07 | 1.11 |
| Reaction tube 21a | 1.06 | 1.11 |
| Reaction tube 31a | 1.04 | 1.03 |
| Reaction tube 38a | 1.05 | 1.03 |

The installation of the seal plate in the baffle plate portion remarkably uniformed the pressure drop, and also reduced the pressure drop, more than in Example 1.

In these Examples, the results were obtained with respect to one row of the reaction tubes arranged from the radial center of the reactor to the shell side. However, in this reactor as above-mentioned, the heat medium is circulated by means of introducing the medium thereinto from almost the whole area of the inner periphery of the reactor by use of a pair of upper and lower annular conduits, and withdrawing the media from almost the whole area of the inner periphery of the reactor. Therefore, it is thought that the same results can be obtained all over the transverse plane of the reactor.

Moreover, in the present invention the level of the pressure drop is almost the same from the radial center of the reactor to the shell side, and the amount of sublimation of the catalyst component is uniform as a whole. Therefore, it is thought that the deterioration of the catalyst is almost the same as a whole. When deterioration of the catalyst locally occurs, the exchange of the whole catalyst depends on the deteriorated area of the catalyst. However, when the level of the deterioration of the catalyst is uniform over the whole area, it can be said that the lifetime of the catalyst relatively becomes long.

The entire disclosure of Japanese Patent Application No. 11-374636 filed on Dec. 28, 1999 including specification, claims, drawings and summary are incorporated herein by reference in its entirety.

What is claimed is:

1. A shell-and-tube heat exchanger comprising:
    an expansion joint installed around the periphery of the shell; and
    an invasion-preventing plate against fluid in the shell side attached to the joint, wherein the invation-preventing plate is attached to one of the two connection portions between the joint and the shell for preventing the invasion of fluid into the joint.

2. A heat exchanger according to claim 1 further comprising:
    a shell holding pluralities of tubes with a first tube and second tube sheets;
    a raw material inlet installed in the first tube sheet side of the shell;
    a product outlet installed in the second tube sheet side of the shell; and
    a baffle plate installed horizontally in the shell.

3. A heat exchanger according to claim 1, wherein the expansion joint is a long circular band having a semicircular-like cross section connected to the shell which was almost horizontally cut.

4. A heat exchanger according to claim 1 further comprising:
    a baffle plate being installed horizontally in the shell.

5. A heat exchanger according to claim 4, wherein the baffle plate includes a donut baffle and disc baffle plates.

6. A heat exchanger according to claim 4, wherein the expansion joint being attached between the baffle plates.

7. A heat exchanger according to claim 1 further comprising:
    a seal plate for fluid in the shell side between the shell wall and a baffle plate being installed horizontally in the shell.

8. A heat exchanger according to claim 1 further comprising:
    a pair of annular conduits having a plurality of openings to introduce and withdraw a fluid in the shell provided with around the shell.

9. A reactor comprising a shell of the shell and tube type heat exchanger according to claim 1 being partitioned into two or more chambers by use of one or more shield sheets transversely of the length of the reaction tube.

10. A method of catalyst gas phase oxidation reaction, which comprises preparing a shell-and-tube heat exchanger, providing an expansion joint installed around a periphery of the shell, providing an invasion-preventing plate against fluid in the shell side attached to the joint for preventing the invasion of fluid into the joint and conducting the reaction in said heat exchanger.

11. A method according to claim 10, wherein the catalytic gas phase oxidation reaction is a reaction of acrolein from propylene in the presence of a catalyst.

* * * * *